United States Patent
Thiruppathi (10) Patent No.: US 7,275,267 B2
(45) Date of Patent: Oct. 2, 2007

(54) TENNIS GLOVE

(76) Inventor: Devaraj Thiruppathi, 4825 Beverly Ave. NE., Canton, OH (US) 44714

( * ) Notice: Subject to any disclaimer, the term of this patent is extended or adjusted under 35 U.S.C. 154(b) by 0 days.

(21) Appl. No.: 10/260,635

(22) Filed: Sep. 30, 2002

(65) Prior Publication Data

US 2004/0060096 A1 Apr. 1, 2004

(51) Int. Cl.
*A41D 19/00* (2006.01)
(52) U.S. Cl. .............................. 2/161.1; 2/160
(58) Field of Classification Search .................. 2/16, 2/20, 160, 161.1–161.6, 163, 170, 21
See application file for complete search history.

(56) References Cited

U.S. PATENT DOCUMENTS

| 1,716,221 | A | * | 6/1929 | Fernie | 2/166 |
| 4,730,354 | A | * | 3/1988 | Saito | 2/161.2 |
| 4,905,321 | A | * | 3/1990 | Walunga | 2/161.1 |
| 5,195,188 | A | * | 3/1993 | Bourdeau et al. | 2/161.1 |
| 5,513,391 | A | * | 5/1996 | Garneau et al. | 2/161.1 |
| 5,517,694 | A | * | 5/1996 | Fabry | 2/161.1 |
| 6,009,557 | A | * | 1/2000 | Witta | 2/159 |

* cited by examiner

*Primary Examiner*—Katherine M. Moran
(74) *Attorney, Agent, or Firm*—Sand + Sebolt (57) ABSTRACT

An athletic glove for racquet sports in specific for the game of tennis, which includes a elastic straps permanently fixed at one end between the thumb and index finger and non-permanently fixed at the other end to the rear wrist cuff. The glove covers the thumb and index finger, leaving the middle finger, ring finger and little finger uncovered whereby, giving the player tactility in feeling the racquet and not hinder the game, at the same time giving the stability to the wrist of player. The glove extends slightly over the palm and back of the hand and is secured to the hand around the wrist area by a strap of the like.

1 Claim, 11 Drawing Sheets

TENNIS GLOVE

FIELD OF THE INVENTION

The present invention relates to gloves, particularly gloves used for playing the game of tennis. More particularly, the present invention relates to a glove having only a thumb and index finger portion and having elastic straps permanently fixed at one end between the thumb and index finger portions and non-permanently fixed at the other end to the rear wrist cuff. Having the thumb and index finger covered while leaving the other three fingers uncovered and having the palm and back of hand partially exposed, allows for tactile feel between the racquet and player whereby control over the stroke is maximized.

BACKGROUND OF THE INVENTION

Various types of gloves have been created with unique strap configuration for a particular activity. Straps have been used to hold the hand firmly to the handles of golf clubs and others to hold securely the fingers and thumb of hand. Billiard gloves have been designed to cover the thumb and first two fingers. Golf gloves have been designed to cover the fingers and expose the palm to obtain greater feel of the swings. There has not been a glove designed for racquet sports particularly for tennis which has adjustable elastic straps on the glove to reduce the head weight of racquet while having the glove cover the thumb and index finger and partially covers the palm and back of hand while leaving the other three fingers and bottom portion of the palm and back of hand exposed. The present invention is designed for racquet sports such as tennis. Tennis is a demanding game and requires a lot of wrist strength. The wrist has to be strong enough to withstand the force of the ball as well as the force of gravity working on the racquet during the duration of the activity. Thus it is desirable to provide an athletic glove, which allows the wearer to withstand the forces affecting the wrist and allowing the player to maintain the tactile feel of the game and not be inhibited by the glove.

SUMMARY OF THE INVENTION

The present invention is a athletic glove for racquet sports which is designed to provide support for the wrist by reducing the vertical forces felt when holding the racquet in a standard handshake position. The vertical forces are reduced on the wrist by two elastic straps permanently secured onto glove. The elastic straps simulate the muscles which are responsible for moving the wrist, such as the extensor carpi radialis longus and brevis and extensor carpi ulnaris muscles. The first elastic is called the longus elastic strap and is permanently attached between the thumb and the index finger to simulate the extensor carpi radialis longus and brevis muscles. The second elastic strap is called backhand elastic strap and is also permanently attached between the thumb and index finger to simulate the backhand muscle that is responsible for the hand to be pulled up and out whereby aiding in the single handed backhand stroke.

The free end of longus elastic strap affixes on the wrist cuff of glove between the thumb and index finger portion in an adjustable way to give varying degree of support of the wrist and hand. The free end of the backhand elastic support strap also affixes on the wrist cuff of glove on the palm side of the little finger for adjustment to give varying degrees of support of the wrist and hand. Once the elastic support straps are securely attached to the wrist cuff the hand is pulled up and out whereby cocking the wrist up, therefore when holding the racquet the head weight of racquet is reduced on the wrist and hand. The elastic straps do not inhibit the natural forehand and backhand strokes in anyway, it only enhances playability. The support straps does not change or inhibit the natural strokes but only re-enforces the natural strokes and reduces the vertical force of racquet on wrist and gives added spring like support to all the strokes.

The athletic glove of the present invention includes a glove having the thumb and index finger covered and leaving the middle finger, ring finger and little finger uncovered and partially covering a palm portion joined with a partially covered back portion, a rear wrist cuff, and elastic straps permanently secured on one end between the thumb and index figure and non-permanently secured on the other end to a rear wrist cuff. The placement of the permanently secured strap can be thought of as a natural extension of the muscle of the hand and wrist, which is responsible in moving the hand. The glove preferably has a vent extending lengthwise from the wrist cuff part way thorough the length of the glove to the open palm. A fastener, such as a tab secured to the glove on one side of the vent having a hook and loop fastener, such as a VELCRO fastener engaging the other side of the vent, permitting the fit of the glove to be adjusted.

To obtain an aesthetic look to a glove the longus elastic strap and the backhand elastic strap are permanently attached underneath on the inside of glove between the thumb and index finger. The longus elastic strap and the backhand elastic strap travel underneath the glove and protrudes out near the site of attachment such that the end portion is non-permanently attached onto the wrist cuff.

To obtain varying degree of support, there may be a plurality of the longus elastic straps and a plurality of the backhand elastic straps, which can be composed of plurality of materials. The materials may have different degree of elastic properties from very elastic to non-elastic. Increased support may be obtained by adjusting the non-permanently attached end of the elastic strap before or during a game by pulling the elastic strap tightly or loosely and attaching it to the wrist cuff by means of a hook and loop fastener on the elastic strap and wrist cuff.

To protect the hand completely and to obtain a standard feel of the glove, the whole hand can be covered by the glove. All the fingers, the index finger, middle finger, ring finger and little finger and thumb can be covered, as well as, a full palm and full back piece. The longus elastic strap and the backhand elastic strap can be permanently attached underneath the glove between the thumb and index finger while traveling underneath on the inside of glove and protrude out near the site of attachment such that the end portion non-permanently attaches onto the wrist cuff. To protect the hand and prevent blisters to the palm and still retain the natural feel of the game, the palm and back piece have full coverage while leaving the little finger, ring finger and middle finger uncovered and fully covering only the index finger and thumb.

Therefore, in accordance with present invention the athletic glove for racquet sports reduces the vertical force produced by the head of racquet and in direct relation improves the backhand and forehand strokes, volleys, backhand returns and backhand slices. The player is less likely with the glove to make an error due to a weak wrist or fatigue due to a long duration of the game, which may compromise the correct form of the strokes.

These and other objects, features and advantages of the present invention will become apparent from the following detailed description. It should be understood, however, that the detailed description and the specific examples, while indicating preferred embodiments of the invention, are given by way of illustrations only, since various changes and modifications within the spirit and scope of the invention will become apparent to those skilled in the art.

BRIEF DESCRIPTION OF THE DRAWINGS

The present invention will become more fully understood from the detailed description given herein below and the accompanying drawings, which are given by way of illustration only and are not limitative of the present invention, wherein.

DETAILED DESCRIPTION OF THE PREFERRED EMBODIMENT

Figure 1:
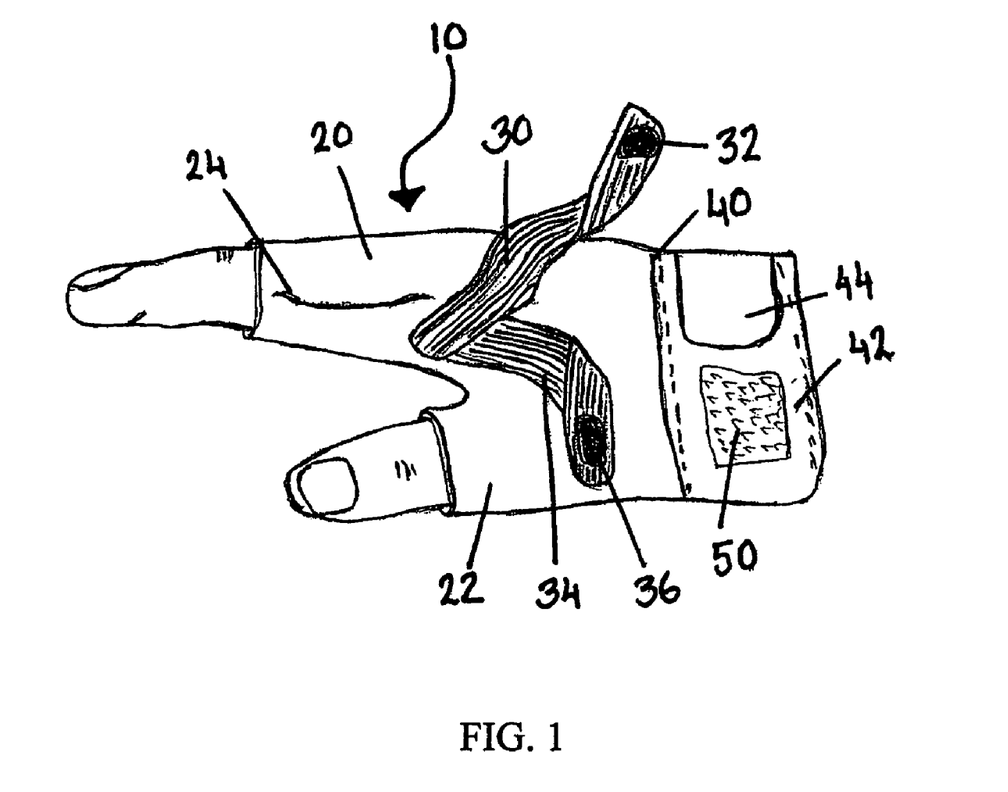
FIG. 1 is an elevated view of glove with elastic straps disengaged in a handshake position.

Referring now to the drawings wherein the depictions are for purposes of illustrating a preferred embodiment of the present invention only and not for the purpose of limiting the same. FIG. 1 is an elevated view of a glove 10 of the present invention. Glove 10 is generally composed of a palm piece 60, a back piece 62, a longus elastic straps 30, a backhand elastic strap 34 and a wrist cuff 42. Glove 10 is adapted to snugly fit the human hand such that palm piece 60 in FIG. 3 lies tightly against the palm of hand while back piece 62 in FIG. 2 lies tightly against the back of hand. Palm piece 60 and back piece 62 are preferably joined by at least one seam, a seam 24, in a conventional continuous manner around the glove as depicted in FIG. 1. When palm piece 60 and back piece 62 are joined, a wrist edge 40 and a index finger portion 20 and a thumb portion 22 are provided in a conventional manner in FIG. 1. It will be understood that although the half-finger portion glove is illustrated, the half finger portion could be replaced with full finger portion, no finger portion or a variety in-between.

Figure 2:
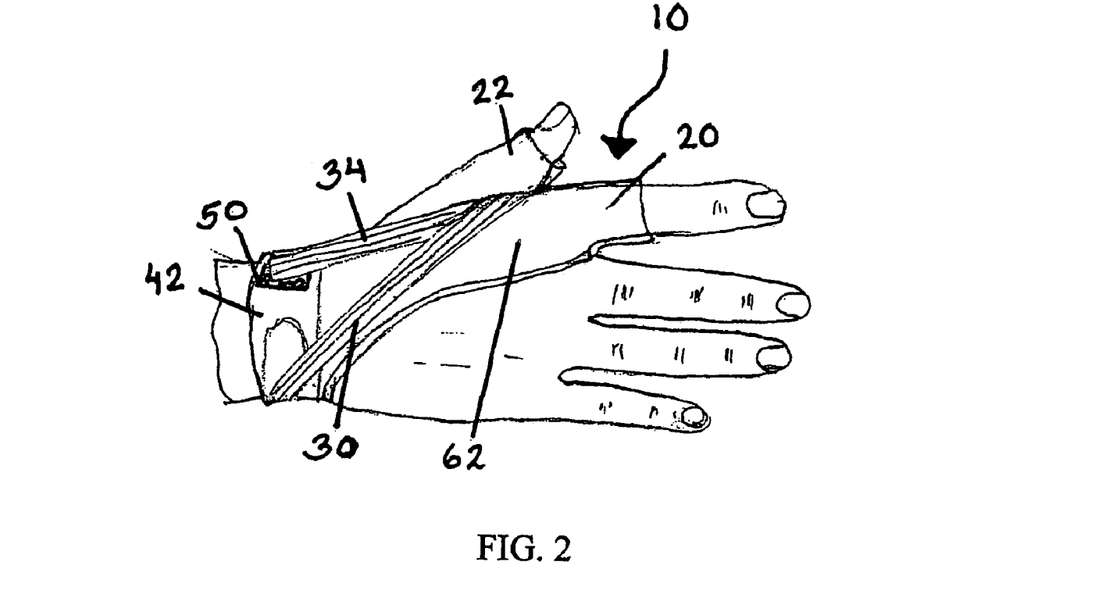
FIG. 2 is a plan view of the backside of glove with elastic straps engaged.
Figure 3:
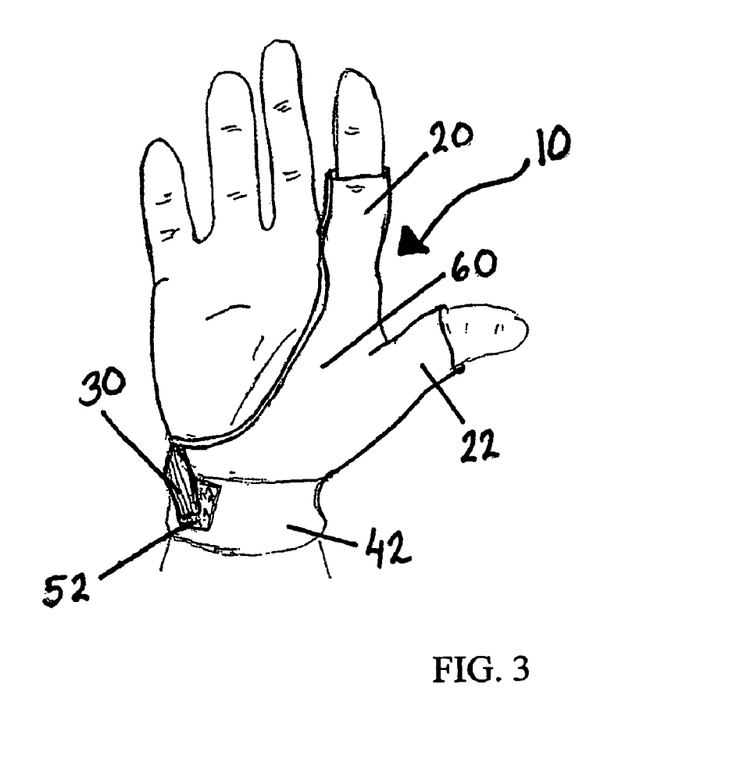
FIG. 3 is a plan view of the palm side of glove with elastic straps engaged.

The palm piece 60 and back piece 62 only cover a portion of the palm the back of hand in FIG. 2 and FIG. 3. This partial covering of the palm allows tennis player the natural feel of the tennis racquet when holding it. The exposed middle finger, ring finger and little finger are referred to as the gripping finger in tennis and are responsible for a strong stable grip in holding the racquet. The index finger and the thumb are referred to as the pinching fingers and are not responsible for the strong grip. The exposed gripping fingers and the partial exposed palm and back is what allow the tennis player to feel the natural feel of the tennis racquet while having the benefits of the snug feel and stable wrist of wearing glove 10.

Figure 4:
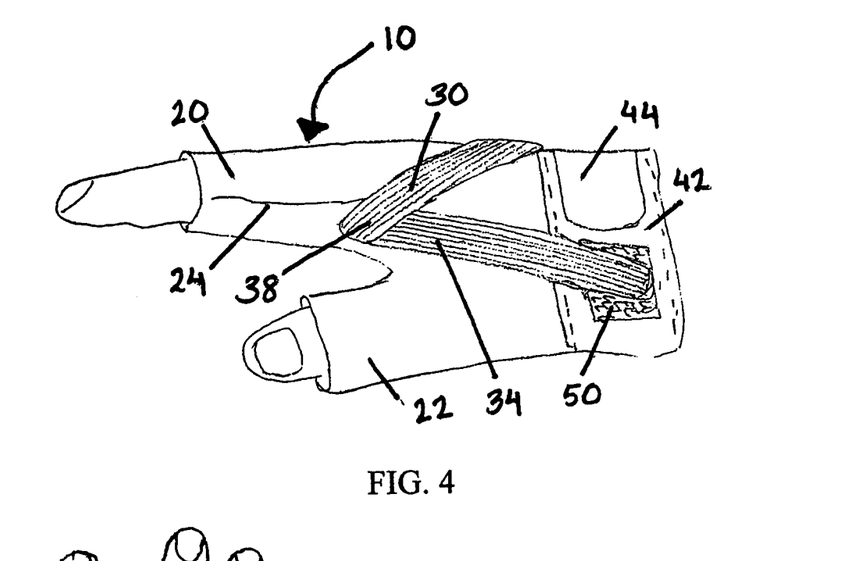
FIG. 4 is an elevated view of glove with elastic straps engaged in a handshake position.

FIG. 4 depicts the elevated view of glove 10 in which the elastic straps are engaged.

Backhand elastic strap 30 and longus elastic strap 34 are permanently fixed at a point 38 between index finger portion 20 and thumb portion 22. FIG. 1 depicts the free end of longus elastic strap 34 comprises a loop element 36 of a hook and loop fastener, such as a VELCRO fastener, sewn to the bottom side thereof. Loop element 36 is for adjustable engagement with a hook element 50 sewn on the outside of wrist cuff 42 between the index finger portion 20 and thumb portion 22. Backhand elastic strap 30 comprises a loop element 32 of a hook and loop fastener, such as a VELCRO fastener, sewn to the bottom side thereof. Loop element 32 is for adjustable engagement with a hook element 52 located on the palm side closer the open side of palm and sewn on the outside of wrist cuff 42 in FIG. 3. Once longus elastic strap 34 is engaged the player will feel the vertical support against gravity of the longus elastic strap 34 whereby the wrist is slightly pulled upward and backward. This added tension caused by longus elastic strap 34 will give increased support to the wrist of the player when holding the racquet, which can be seen and felt by the stretching of longus elastic strap 34, acting like a loaded spring helping the player lift the racquet quickly and stabilizing the wrist. Once backhand elastic strap 30 is engaged the player will feel the backhand support of backhand elastic strap 30 whereby slightly pulling the back of hand back. This added tension caused by backhand elastic strap 30 will give increased support to the wrist of the player when the player takes the racquet back for a backhand swing and bends the wrist slightly forward or inward to hit the backhand shot, which can be seen and felt by the stretching of backward elastic strap 30 which acts like a loaded spring flicking the wrist back.

Figure 5:
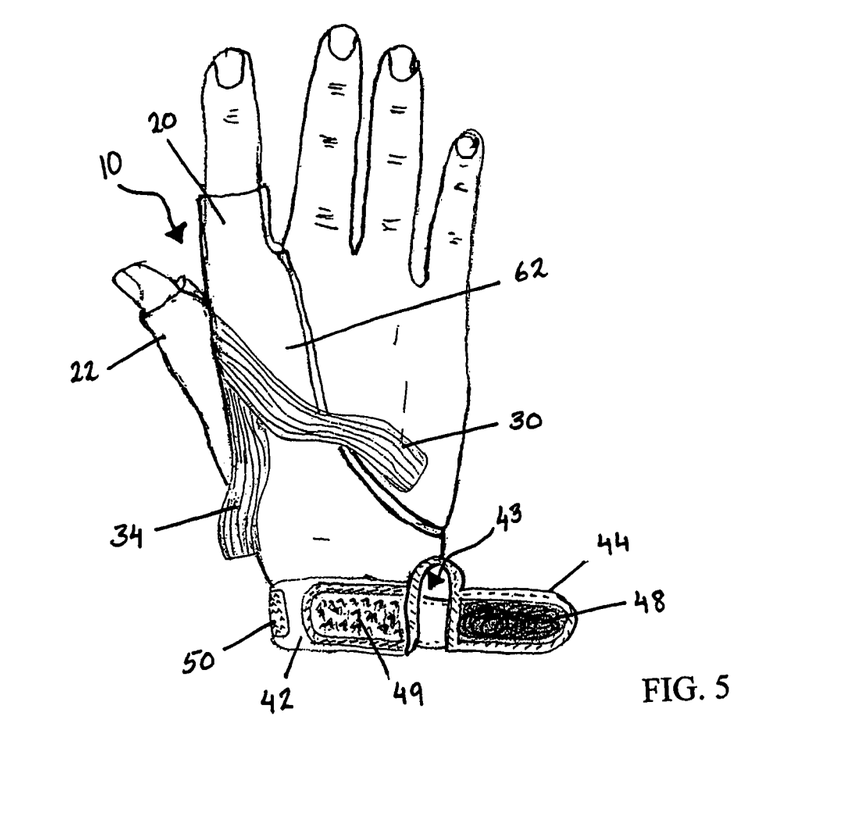
FIG. 5 is a plan view of backside of glove with elastic straps disengaged and wrist cuff open.

FIG. 5 depicts wrist cuff 42 which forms the lower portion of glove 10 adjacent to the hand opening on both the palm side and back side, and is constructed of elastic and non-elastic material to provide stability to the wrist. Glove 10 has a slit 43 therein which extends from wrist cuff 42 short way through the length of glove on the opposite side of thumb portion 22 and between palm piece 60 and back piece 62. Wrist cuff 42 includes a lateral tab 44 sewn directly to the palm portion of the wrist cuff along a lengthwise seam of the split. Tab 44 comprises a loop element 48 of a hook and loop fastener, such as a VELCRO fastener, sewn to the inside thereof. Loop element 48 is for adjustable engagement with a hook element 49 sewn to the outside back portion of wrist cuff 42.

Figure 6:
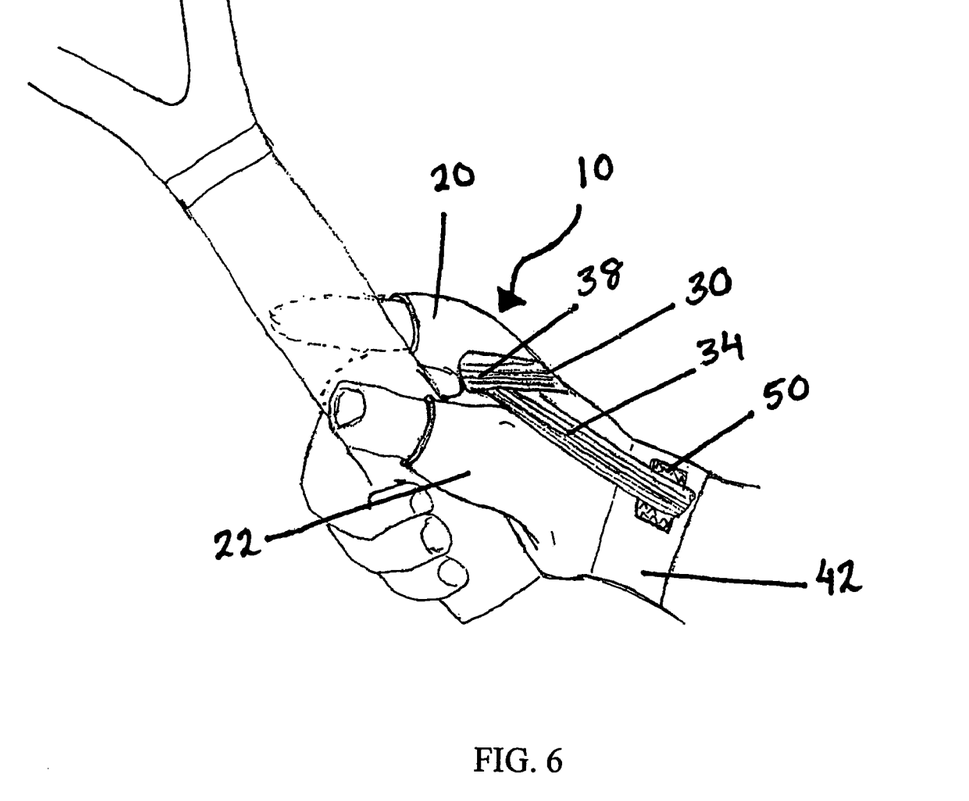
FIG. 6 is a diagrammatic view of glove with the hand gripping the handle portion of a tennis racquet.
Figure 7:
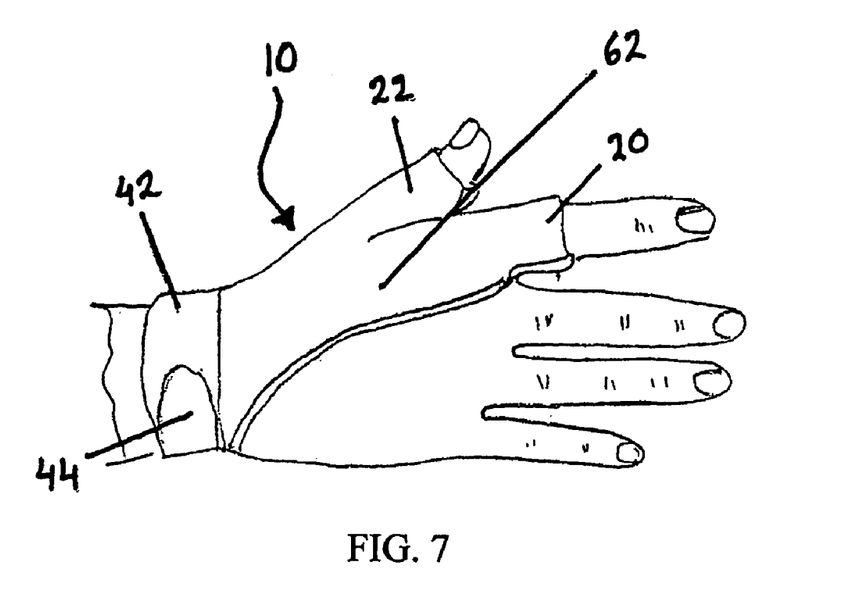
FIG. 7 is a plan view of the backside of glove.
Figure 8:
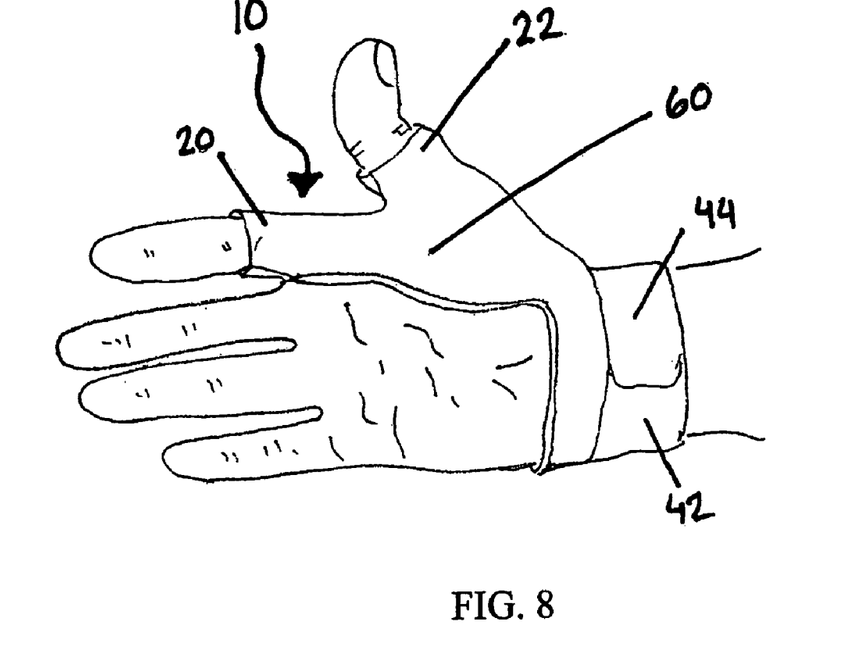
FIG. 8 is a plan view of the palm side of glove.
Figure 9:
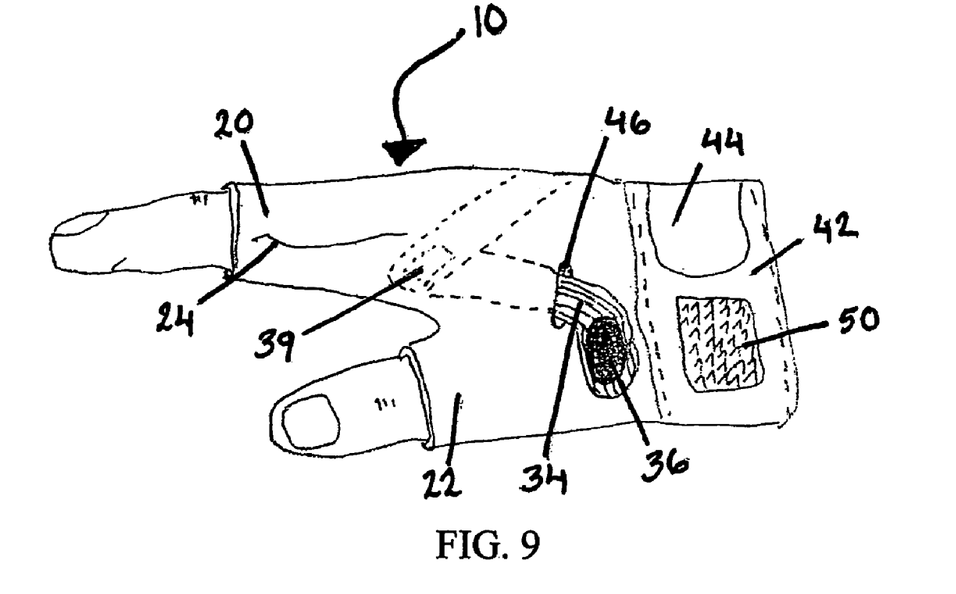
FIG. 9 is an elevated view of glove elastic straps disengaged and attached to the underside of glove.
Figure 10:
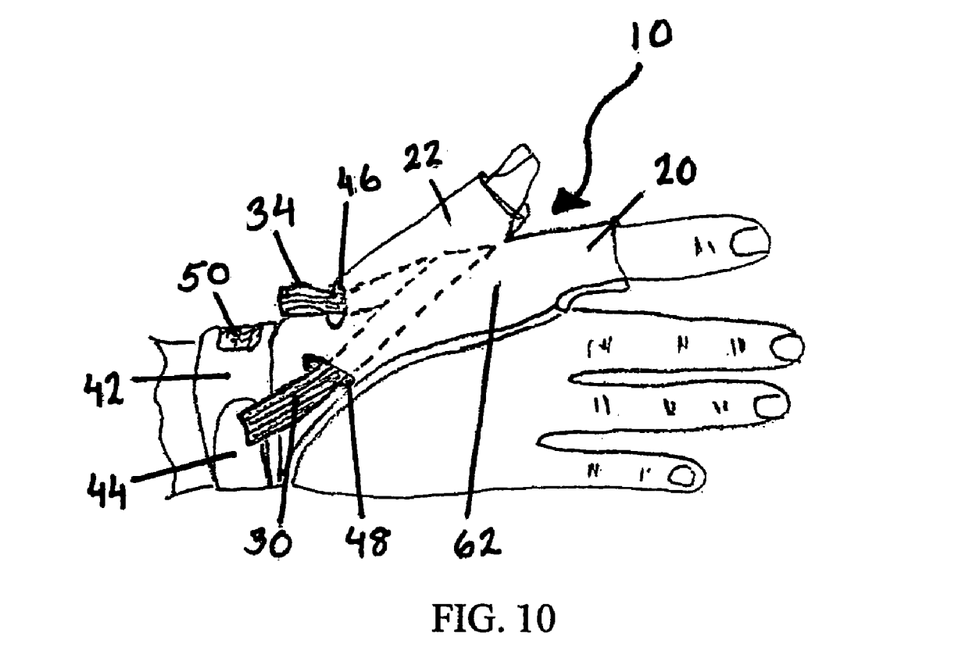
FIG. 10 is a plan view of backside of glove with elastic straps disengaged and attached to the underside of glove.
Figure 11:
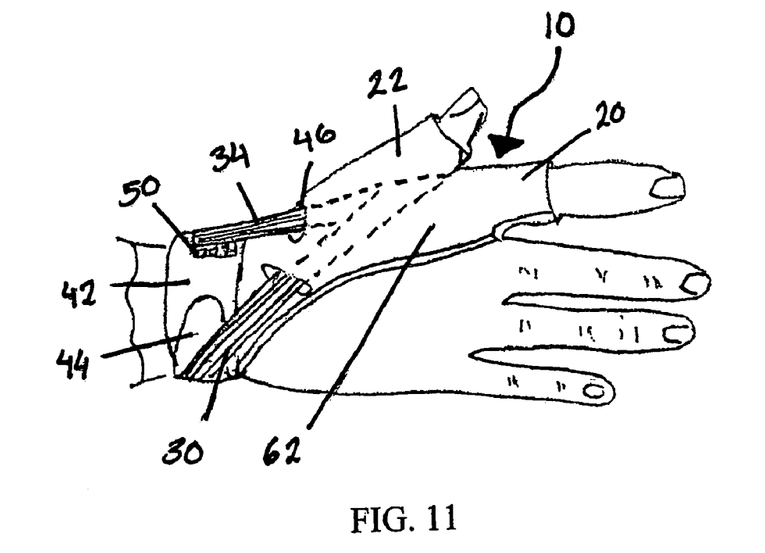
FIG. 11 is a plan view of backside of glove with elastic straps engaged and attached to the underside of glove.
Figure 12:
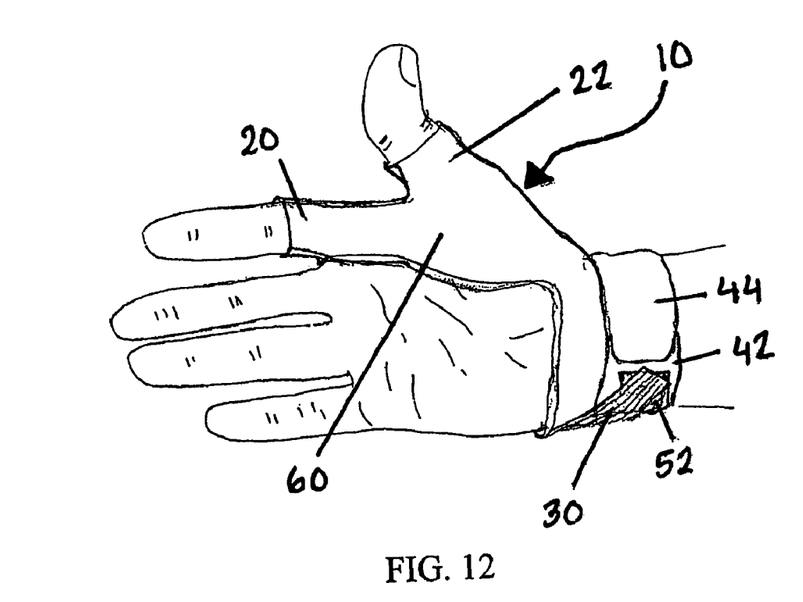
FIG. 12 is a plan view of the palm side glove with elastic straps engaged and attached to the underside of glove.

FIG. 6 is a diagrammatical view of a hand wearing glove 10 and holding the racquet with the backhand elastic strap 30 and longus elastic strap 34 engaged. The glove allows for a spring like support of the racquet being held and reduces the vertical gravitational force of the racquet being held. FIG. 7 and FIG. 8 represents glove 10 without the elastic straps attached to glove. This type of glove configuration allows the player the natural feel of the racquet and the firm support of a glove supporting the wrist and hand. Glove 10 has the index finger portion 20 and the thumb portion 22 with the partial covered back piece 62 and the partial covered palm piece 60 and the wrist cuff 42 with the wrist tab 44 for adjustable engagement comprising of a hook and loop fastener. FIG. 9 is an elevated view of glove 10 with the backhand elastic strap 30 and longus elastic strap 34 attached inside of glove 10 at a location 39 between the index finger portion 20 and thumb portion 22. Longus elastic strap 34 runs along the inside of glove and come out of a longus opening 46 and attach to the hook fastener 50 located on wrist cuff 42 by loop fastener 36 permanently attached to longus elastic strap 34. FIG. 10 depicts the backside of glove 10 with backhand elastic strap 30 and longus elastic strap 34 disengaged. Backhand elastic strap 30 travels along the inside of glove 10 and come out of a backhand opening 48 located on the back piece 62. FIG. 11 depicts the fastening of longus elastic strap 34 to the hook element 50 of a hook and loop fastener located on wrist cuff 42. FIG. 12 depicts the fastening of backhand elastic strap 30 to the hook element 52 of a hook and loop fastener located on wrist cuff 42 on the palm piece 60.

Figure 13:
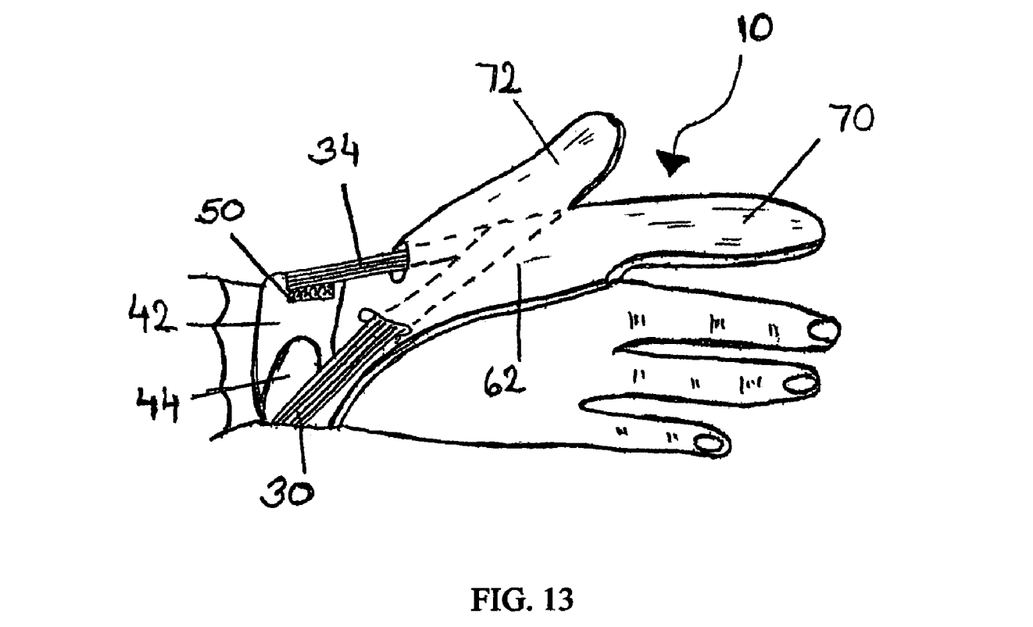
FIG. 13 is a plan view of backside of glove with a partially covered back and palm with one finger and thumb covered fully with elastic straps engaged and attached to the wrist cuff of glove.

Another embodiment of glove 10 is FIG. 13 representing the glove covering the index finger and thumb completely with a full finger 70 and a full thumb 72 with the fastening of longus elastic strap 34 to the hook element 50 of a hook and loop fastener located on wrist cuff 42.

Figure 14:
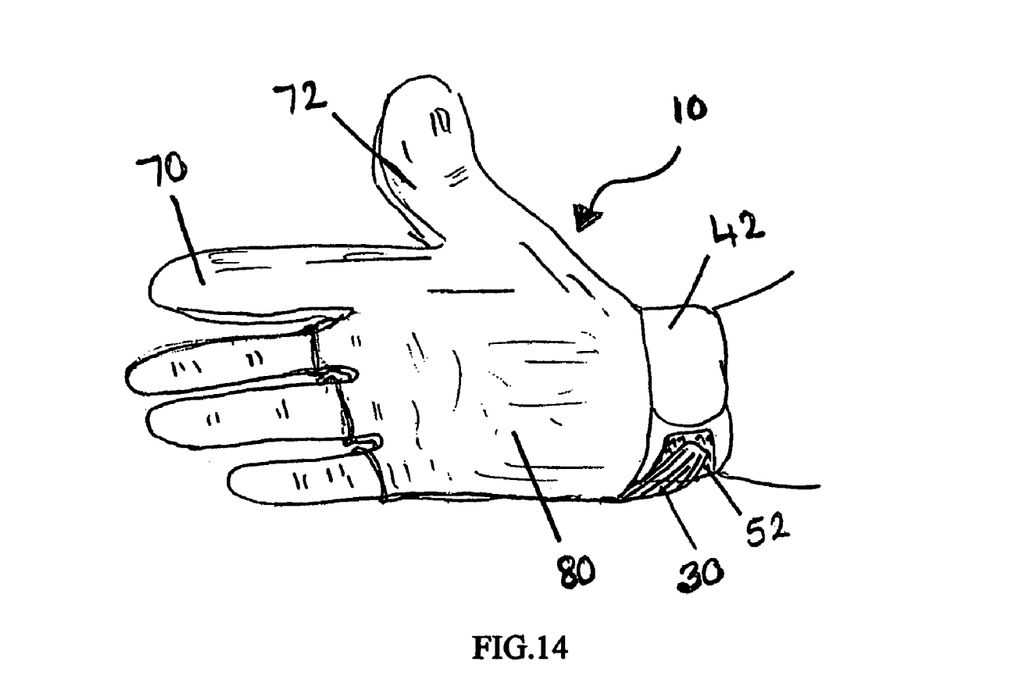
FIG. 14 is a plan view of palm side of glove with a fully covered palm with one finger and thumb covered fully with elastic straps engaged and attached to the wrist cuff of glove.
Figure 15:
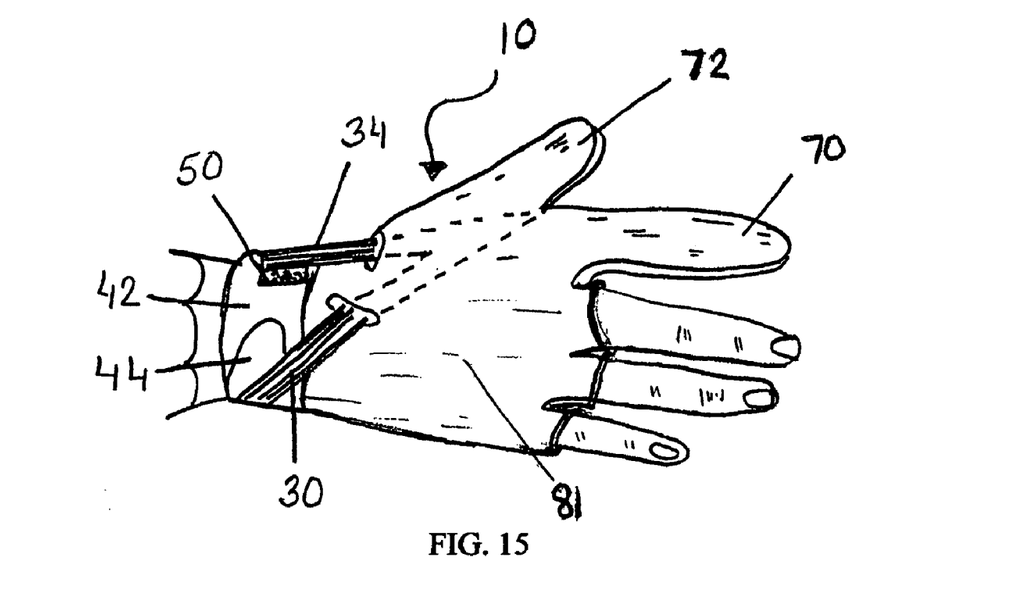
FIG. 15 is a plan view of back side of glove with a fully covered back with one finger and thumb covered fully with elastic straps engaged and attached to the wrist cuff of glove.

Yet another embodiment of glove 10 is FIG. 14 representing the glove fully covering the backhand and palm with a full palm piece 80 and the full finger 70 and full thumb 72 with backhand elastic strap 30 engaged to the hook element 52 of a hook and loop fastener located on wrist cuff 42. FIG. 15 represents the glove with a full back piece 81 and the full finger 70, full thumb 72 with the fastening of longus elastic strap 34 to the hook element 50 of a hook and loop fastener located on wrist cuff 42.

Figure 16:
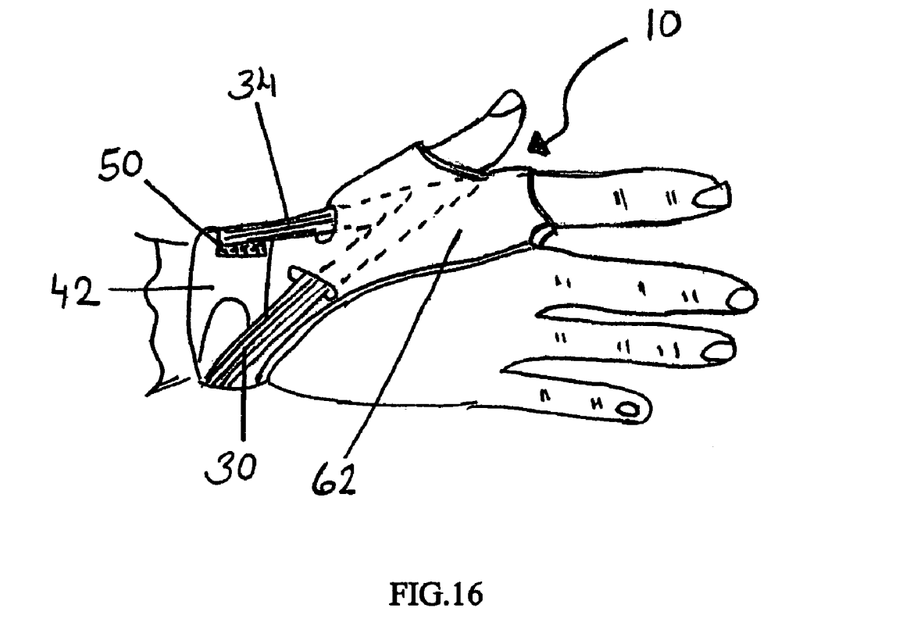
FIG. 16 is a plan view of backside of glove with a partially covered palm and back with the thumb and index finger having no coverage.
Figure 17:
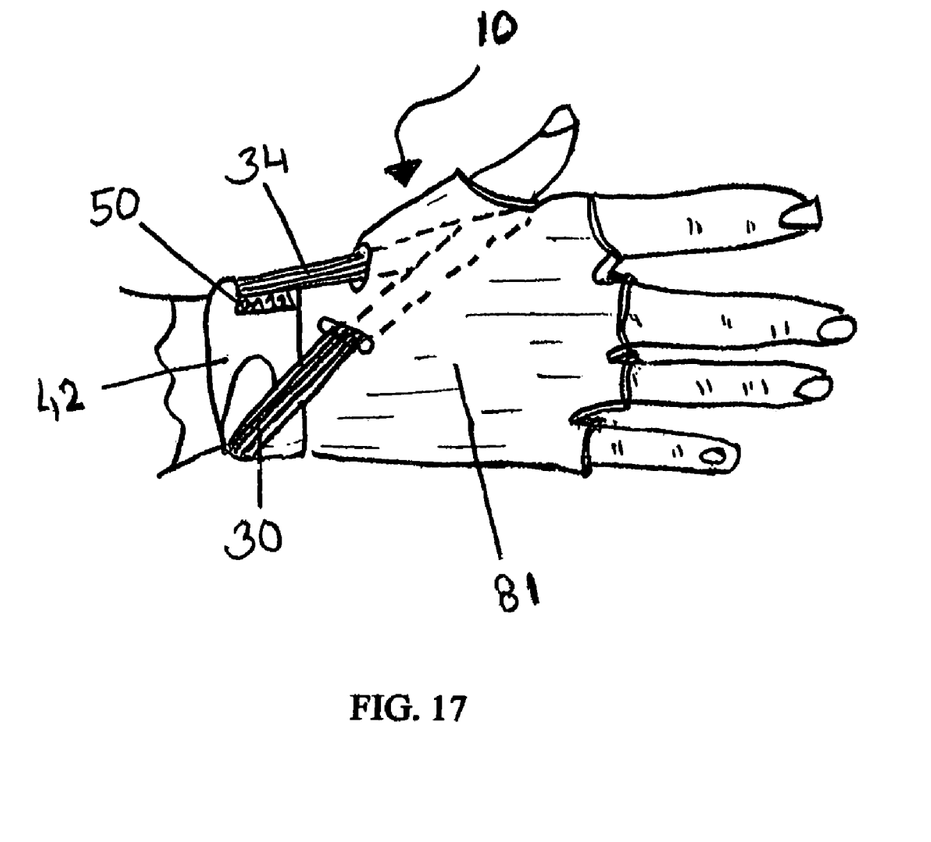
FIG. 17 is a plan view of back side of glove with a fully covered back and palm with the thumb and index finger having no coverage.

FIG. 16 is another embodiment of glove 10 with the partially covered back and palm piece with the thumb and index finger not covered depicting the partial covered back piece 62. The longus elastic strap 34 is fastened to the hook element 50 of a hook and loop fastener located on wrist cuff 42. Yet another embodiment of glove 10 is FIG. 17 with the fully covered palm and a full back piece 81 and having no coverage of the thumb and index finger with the longus elastic strap 34 engaged to the hook element 50 of a hook and loop fastener located on wrist cuff 42.

Figure 18:
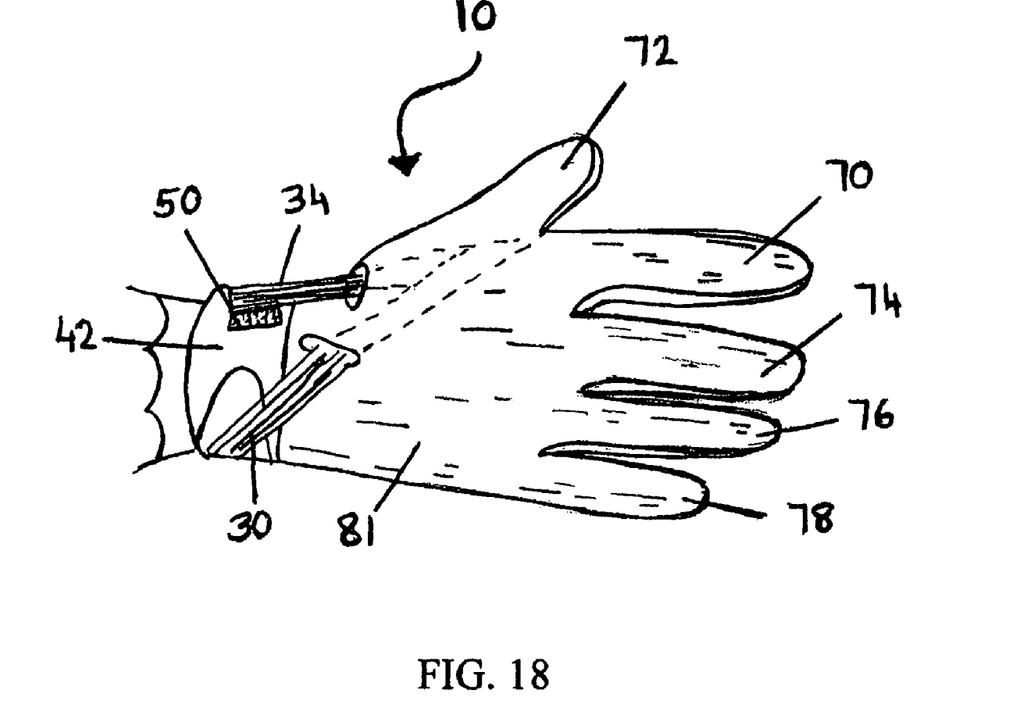
FIG. 18 is a plan view of back side of glove with all the fingers, thumb, palm and back fully covered with the elastic straps engaged and attached to the wrist cuff.

Yet another embodiment of glove 10 is FIG. 18 representing the glove fully covering all the fingers, full finger 70, full middle finger 74, full ring finger 76, full little finger 78 and full thumb 72 with a fully covered back piece 81. FIG. 18 depicts the fastening of longus elastic strap 34 to the hook element 50 of a hook and loop fastener located on wrist cuff 42 and the engagement of the backhand elastic strap 30 to wrist cuff 42.

What is claimed is:

1. A glove used to support the wrist and help support the weight of a racquet while preserving the natural feel of the racquet: said glove comprising an interior surface, exterior surface, index finger portion, thumb portion, a partial palm piece and a partial back piece, a first elastic strap with first and second ends, a second elastic strap with first and second ends, and a wrist cuff with a first and second hook and loop attachment means; wherein the first elastic strap is attached to the interior surface of said glove by stitching said first end of the strap at a location on the back piece between said index finger portion and said thumb portion, said second end of said first elastic strap including a hook and loop attachment means, said back piece including first and second apertures; whereby the second end of the first strap extends through said first aperture and is removably attachable to the first hook and loop attachment means positioned on the wrist cuff, a second elastic strap also stitched at a first end thereof to the interior surface at the location on the back piece between said index finger portion and said thumb portion, whereby the second end of the second strap extends through said second aperture and is removably attachable to the second hook and loop attachment means positioned on the wrist cuff.

* * * * *